United States Patent [19]

Moore et al.

[11] Patent Number: 5,877,360
[45] Date of Patent: Mar. 2, 1999

[54] CHEMICAL PROCESS

[75] Inventors: Geoffrey James Moore, Northwich; Jenny O'Kell, Sale, both of England

[73] Assignee: Imperial Chemical Industries PLC, London, England

[21] Appl. No.: 352,448

[22] Filed: Dec. 9, 1994

Related U.S. Application Data

[63] Continuation of Ser. No. 130,411, Oct. 1, 1993, abandoned, which is a continuation of Ser. No. 864,409, Apr. 6, 1992, abandoned.

[30] Foreign Application Priority Data

Apr. 11, 1991 [GB] United Kingdom ................... 9107677

[51] Int. Cl.⁶ .................................................. C07C 19/08
[52] U.S. Cl. ............................................................ 570/176
[58] Field of Search ............................................. 570/176

[56] References Cited

FOREIGN PATENT DOCUMENTS

| | | | |
|---|---|---|---|
| 670338 | 9/1983 | Canada | 570/176 |
| 0347830 | 12/1989 | European Pat. Off. . | |
| 0379793 | 8/1990 | European Pat. Off. . | |
| 1206424 | 12/1965 | Germany . | |
| 9008748 | 8/1990 | WIPO | 570/176 |

OTHER PUBLICATIONS

Park et al., Thermochemical & Photochemical Studies on Organic Fluorine Compounds, AFOSR Document No. TR–58–99. ASTIA No. AD 162 198, Dept. of Chemistry, University of Colorado.

*Primary Examiner*—Alan Siegel
*Attorney, Agent, or Firm*—Pillsbury Madison & Sutro LLP

[57] ABSTRACT

A process for the production of difluoromethane which comprises reacting a compound of formula $XYCF_2$ wherein X and Y are each H, Cl or Br but at least one of X and Y is an atom other than hydrogen, and in particular chlorodifluoromethane, with hydrogen at elevated temperature in the presence of a hydrogenation catalyst, in particular a catalyst comprising palladium carried on an active carbon support.

8 Claims, No Drawings

CHEMICAL PROCESS

This is a continuation of application Ser. No. 08/130,411, filed on Oct. 1, 1993, now abandoned which is a continuation of U.S. Pat. No. 07/864,409, filed Apr. 6, 1992, now abandoned.

This invention relates to a process for the production of difluoromethane.

In recent years chlorofluorocarbons, which are used on a large scale around the world, have been perceived as having an adverse effect on the ozone layer and/or as contributing to global warming. Chlorofluorocarbons are used, for example, as refrigerants, as foam blowing agents, as cleaning solvents and as propellants for aerosol sprays in which the variety of applications is virtually unlimited. Consequently, much effort is being devoted to finding suitable replacements for chlorofluorocarbons which will perform satisfactorily in the many applications in which chlorofluorocarbons are used but which will not have the aforementioned environmentally harmful effects. One approach in the search for suitable replacements has centred on fluorocarbons which do not contain chlorine but which may contain hydrogen. The hydrofluorocarbon difluoromethane, also known as HFA 32, is of interest as one such replacement, in particular as a replacement in refrigeration, air-conditioning and other applications.

According to the present invention there is provided a process for the production of difluoromethane which comprises reacting a compound of formula $XYCF_2$ wherein X and Y are each H, Cl or Br but at least one of X and Y is an atom other than hydrogen, with hydrogen at elevated temperature in the presence of a hydrogenation catalyst.

The process may be conveniently effected by feeding a stream comprising the compound of formula $XYCF_2$ and hydrogen, as a combined or as separate streams through a vessel containing the hydrogenation catalyst.

The starting compounds of formula $XYCF_2$ are dichlorodifluoromethane, dibromodifluoromethane, chlorobromodifluoromethane, chlorodifluoromethane and bromodifluoromethane. Mixtures of the above compounds may be employed. Usually the compound of formula $XYCF_2$ will be a chlorinated difluoromethane and chlorodifluoromethane is the preferred starting compound.

Where the compound of formula $XYCF_2$ is chlorodifluoromethane, we have found that the yield of difluoromethane is dependent upon the catalyst composition, temperature and pressure, and that these parameters may be selected to give surprisingly high yields of difluoromethane, and in particular, substantially higher yields of difluoromethane than the yields which have previously been achieved by hydrogenation of chlorine-containing difluoromethanes.

Accordingly the present invention further provides a process for the production of difluoromethane which comprises contacting chlorodifluoromethane with hydrogen in the presence of a hydrogenation catalyst wherein the temperature, pressure and catalyst composition are such that difluoromethane is produced with a yield of at least 20%. Preferably the yield is at least 25%, more preferably at least 30% and especially at least 35%.

Hydrogenation catalysts are in themselves well known. Examples of hydrogenation catalysts include nickel or metals of Group VIIIa of the Periodic Table, for example platinum, ruthenium, osmium, iridium and rhodium, or oxides or salts thereof. In use, a compound of such a metal is reduced at least in part to the metal. One very useful metal which can be employed is palladium, and we prefer to employ a catalyst which comprises palladium. The metal may, and usually will, be carried on a suitable support, for example, alumina, silica or carbon. A particularly preferred metal/support combination is palladium on an active carbon.

Furthermore, the catalyst may comprise more than one metal which may be carried on a suitable support. Where more than one metal is carried on the support, we generally prefer that one of the metals is palladium. The other metal is preferably a more active hydrogenation catalyst than palladium and the other metal serves to hydrogenate any chlorofluoromethane which may be produced by the process, and which is a toxic impurity, to methane. We have found that the provision of a metal other than palladium, in addition to palladium, may reduce the level of chlorofluoromethane in the product stream without significantly reducing the overall yield of difluoromethane. Thus,. the provision of a more active hydrogenation catalyst than palladium, in addition to palladium, acts to purify the product stream by hydrogenation of the toxic impurity, chlorofluoromethane, to methane.

The catalyst may comprise palladium and one or more other group VIIIa metals, for example ruthenium, rhodium or nickel, or other metals, for example silver or chromium, carried on a suitable support. A particularly preferred catalyst comprises palladium and nickel, since we have found that a catalyst comprising palladium and nickel has a profound effect in reducing the amount of the toxic impurity chlorofluoromethane which is present in the product stream. The palladium and nickel may be carried on a support, preferably an active carbon. Each may be carried on the same support, for example an active carbon or on different active carbon supports. Where they are carried on the same support, they may be present as an alloy, if desired.

We have also found that where the support is an active carbon, the overall yield of difluoromethane is profoundly influenced by the particular active carbon which is employed.

According to a further aspect of the present invention there is provided a process for the production of difluoromethane which comprises contacting chlorodifluoromethane with hydrogen in the presence of a catalyst comprising palladium carried on an active carbon support at elevated temperature wherein the active carbon is such that at a temperature of 300° C., at atmospheric pressure, with a 2:1 molar excess of hydrogen to chlorofluoromethane and with a palladium loading on the active carbon of 8% w/w (whether or not other metals are also present), the yield of difluoromethane is at least 20%. Preferably the yield of difluoromethane is at least 25%, more preferably at least 30% and especially at least 35%.

Whilst it is believed that an important characteristic of the active carbon in determining its effectiveness is the surface area of the carbon, it is clear that other factors are also important including for example acidity, bulk density, the presence of impregnants, the nature of the carbon which is activated and its method of manufacture. Certain active carbons have a demonstrable effect upon the selectivity of the catalyst towards the production of difluoromethane. One type of active carbon which we have found particularly preferably is active carbons which have been manufactured by extrusion.

In the majority of supported catalysts, the loading of the metal on the support material may be dependent at least to some extent on the particular metal catalyst/support combination being used. However the % w/w catalyst to support is typically from about 0.1% w/w to about 40% w/w, and where the catalyst/support combination comprises palladium supported on an active carbon, the % w/w Pd to active carbon is usually from about 5.0% w/w to about 20% w/w, preferably from about 8.0% w/w to about 20% w/w, and especially from about 8% w/w to about 15% w/w.

In the case where a mixed metal catalyst is employed the proportions of the metals present may vary within a wide range, although generally we prefer to employ a catalyst which is based on palladium. Generally we prefer to employ a catalyst in which there is at least twice as much palladium present as other metals. Where the catalyst comprises a mixture of palladium and nickel, we prefer to employ palladium and nickel in the ratio from about 2:1 to about 500:1, and more preferably from about 5:1 to about 100:1. A preferred catalyst comprises from about 0.5% to 20%, in particular from about 5 to 15% w/w palladium and from about 0.05% to about 5%, in particular from about 0.1% to about 2% by weight nickel, supported on an active carbon. Overall the amount of the metal which is a more active hydrogenation catalyst than palladium, is usually in the range from about 0.01% w/w to about 5% w/w.

The proportion of hydrogen to starting compound of formula $XYCF_2$ may be varied considerably. Usually at least the stoichiometric amount of hydrogen is employed to replace the chlorine and/or bromine atom(s), and considerably greater than stoichiometric amounts, for example 4 or more moles of hydrogen per mole of starting compound may be employed. Where X and Y are each chlorine or bromine, it is preferred to employ at least two moles of hydrogen (the stoichiometric amount) per mole of starting compound. Where the starting compound of formula $XYCF_2$ is chlorodifluoromethane it is preferred to employ between 1 and 2 moles of hydrogen per mole of chlorodifluoromethane.

Atmospheric or superatmospheric pressures, for example up to about 60 bars may be employed. We have found that operation of the process of the invention at superatmospheric pressure substantially increases the selectivity of the process towards the production of difluoromethane. The process is preferably operated at a pressure in the range from about 2 bar to about 60 bar and more preferably from about 2 bar to about 30 bar, especially 5 bar to 30 bar.

The reaction is suitably carried out in the vapour phase at a temperature which is at least about 150° C. and not greater than about 450° C., usually from about 225° C. to about 400° C., and preferably from about 240° C. to about 360° C. The most preferred temperature is dependent upon the pressure at which the process is operated; at atmospheric pressure, we prefer to operate the process at a temperature in the range from about 220° C. to about 320° C., whereas at a pressure of about 7.5 bar, we prefer to employ temperatures in the range from about 270° C. to about 360° C.

Contact times are usually in the range 1 to 60 seconds, especially 5 to 30 seconds, when the reaction is carried out in the vapour phase.

In the present process, any unreacted hydrogen and other starting material, together with any organic by-products, may be recycled.

The difluoromethane product may be contaminated with small amounts of by-products, for example chlorofluoromethane, chloromethane, fluoromethane and methane. Many of these by-products may be removed by conventional means, for example by fractional distillation. However, one by-product which may be produced is chlorofluoromethane which must be removed or at least reduced to extremely low levels, for example below 10 ppm, because it is toxic. Although chlorofluoromethane has a different boiling point to that of difluoromethane, so that they may be separated to a high degree by conventional means, for example by distillation, such conventional processes do not sufficiently reduce the levels of the chlorofluoromethane impurity.

We have found that the chlorofluoromethane and other chlorine containing impurities may be removed from the difluoromethane product by contacting the impure difluoromethane with an active carbon.

According to a further embodiment of the invention there is provided a process for the production of difluoromethane which comprises reacting a compound of formula $XYCF_2$ wherein X and Y are each H, Cl or Br but at least one of X and Y is an atom other than hydrogen, with hydrogen at elevated temperature in the presence of a hydrogenation catalyst to produce difluoromethane and wherein chlorocarbon impurities are removed from the difluoromethane by contacting the impure difluoromethane with an active carbon. A preferred embodiment is characterised by the removal of chlorofluoromethane from difluoromethane by contacting the impure difluoromethane with an active carbon.

The invention is illustrated, but not limited, by the following examples.

EXAMPLE 1

60 mls of a catalyst comprising 0.84% w/w palladium supported on charcoal (Grade 208c supplied by Sutcliffe Speakman Ltd) were charged into a heat resistant glass tube reactor of 1 inch internal diameter surrounded by an electric furnace.

Hydrogen and chlorodifluoromethane were passed through the heated tube, the catalyst bed being maintained at an essentially constant temperature. Four runs were carried out at the temperatures shown in Table 1 below. The flow rates of hydrogen and chlorodifluoromethane were 60 ml/minute and 30 ml/minute respectively.

The reactor exit gas was diluted with 300 ml/minute nitrogen and passed through a scrubbing tower of soda lime to remove acid gases. The scrubbed exit gas was then analysed by gas chromatography. The relative amounts of the only organic products detected in the scrubbed exit gas, based upon gas chromatagram peak areas only, were as shown in Table 1.

TABLE 1

| | Temperature/°C. | | | |
|---|---|---|---|---|
| Product. | 261 | 334 | 357 | 386. |
| $CH_2F_2$. | 5.47 | 21.64 | 21.07 | 21.82 |
| $CH_4$. | 2.15 | 31.22 | 44.59 | 57.92 |
| $CF_3H$. | 0.11 | 0.25 | 0.10 | 0.13 |
| $CH_3Cl$. | — | — | 0.24 | 0.42 |
| $CH_3CH_3$. | — | 0.88 | 2.44 | 4.15 |
| $CF_2Cl_2$ | — | — | 0.09 | 0.11 |
| $CH_2FCl$. | — | 0.21 | 0.18 | 0.32 |

EXAMPLE 2

The procedure of example 1 was repeated but with a catalyst comprising 5% w/w palladium supported on Grade 208c charcoal. The composition of the organic products after scrubbing was as shown in Table 2.

TABLE 2

| Product | Temperature/°C. | | | |
|---|---|---|---|---|
| | 210 | 238 | 282 | 316. |
| $CH_2F_2$. | 7.70 | 18.27 | 36.77 | 35.90 |
| $CH_4$. | 1.51 | 5.24 | 28.62 | 54.83 |
| $CF_3H$. | — | — | — | 0.13 |
| $CH_3Cl$. | — | — | — | 0.13 |
| $CH_3CH_3$. | — | — | 0.31 | 0.90 |

EXAMPLE 3

The procedure of example 1 was repeated but with a catalyst comprising 10% w/w palladium supported on Grade 208c charcoal. The composition of the organic products after scrubbing was as shown in Table 3.

TABLE 3

| Product | Temperature/°C. | | | | |
|---|---|---|---|---|---|
| | 217 | 242 | 262 | 294 | 326. |
| $CH_2F_2$. | 8.74 | 18.83 | 29.67 | 39.53 | 39.25 |
| $CH_4$. | 1.65 | 5.70 | 12.86 | 29.73 | 47.03 |
| $CF_3H$. | — | — | — | — | 0.14 |
| $CH_3Cl$. | — | — | — | — | 0.07 |
| $CH_3CH_3$. | — | — | — | 0.34 | 0.90 |

EXAMPLE 4

The procedure of example 1 was repeated but with a catalyst comprising 15% w/w palladium supported on Grade 208c charcoal. The composition of the organic products after scrubbing was as shown in Table 4.

TABLE 4

| Product | Temperature/°C. | | | | |
|---|---|---|---|---|---|
| | 225 | 265 | 297 | 326 | 356 |
| $CH_2F_2$. | 8.13 | 23.76 | 29.30 | 25.62 | 19.98 |
| $CH_4$. | 2.20 | 15.09 | 44.15 | 60.62 | 73.01 |
| $CF_3H$. | — | — | — | 0.11 | 0.08 |
| $CH_3Cl$. | — | — | — | 0.15 | 0.26 |
| $CH_3CH_3$. | — | — | 0.33 | 1.14 | 1.97 |

EXAMPLE 5

The procedure of example 1 was repeated but with a catalyst comprising 20% w/w palladium supported on Grade 208c charcoal. The composition of the organic products after scrubbing was as shown in Table 5.

TABLE 5

| Product | Temperature/°C. | | | |
|---|---|---|---|---|
| | 210 | 238 | 282 | 316 |
| $CH_2F_2$. | 7.7 | 18.3 | 36.8 | 35.9 |
| $CH_4$. | 1.51 | 5.24 | 28.7 | 54.8 |
| $CF_3H$. | — | — | — | 0.13 |
| $CH_3Cl$. | — | — | — | 0.13 |
| $CH_3CH_3$. | — | — | 0.3 | 0.9 |

EXAMPLE 6

The procedure of example 1 was repeated except that the catalyst comprised 10% w/w platinum on an active carbon (Grade 208c supplied by Sutcliffe Speakman). The composition of the organic products after scrubbing was as shown in Table 6.

TABLE 6

| Product | Temperature/°C. | | |
|---|---|---|---|
| | 215 | 255 | 306 |
| $CH_2F_2$. | 0.18 | 0.82 | 5.94 |
| $CF_3H$. | 0.21 | 0.65 | 0.02 |
| $CH_4$. | 0.79 | 3.64 | 43.4 |
| $CH_3Cl$. | — | — | 0.03 |

EXAMPLE 7

The procedure of example 1 was repeated except that a catalyst comprising 5% w/w ruthenium on active carbon was employed (supplied by Engelhard). The composition of the organic products after scrubbing was as shown in Table 7.

TABLE 7

| Product | Temperature/°C. | | |
|---|---|---|---|
| | 211 | 276 | 316 |
| $CH_2F_2$. | 0.27 | 1.46 | 2.15 |
| $CF_3H$. | 0.02 | 0.01 | 0.02 |
| $CH_4$. | 4.29 | 34.01 | 57.6 |
| $CH_3Cl$. | 0.02 | 0.34 | 2.04 |
| $CH_3F$ | 0.02 | 0.04 | 0.02 |
| $CH_2FCl$ | — | 0.04 | 0.01 |

EXAMPLE 8

The procedure of example 1 was repeated except that a catalyst comprising 5% w/w rhodium on an active carbon was employed. The composition of the organic products after scrubbing was as shown in Table 8.

TABLE 8

| Product | Temperature/°C. | | |
|---|---|---|---|
| | 209 | 271 | 313 |
| $CH_2F_2$. | 0.06 | 4.46 | 8.2 |
| $CF_3H$. | 0.01 | 0.12 | 0.08 |
| $CH_4$. | 2.21 | 22.75 | 52.01 |
| $CH_3Cl$. | 0.01 | 0.01 | 0.04 |
| $CH_3F$ | — | 0.01 | 0.02 |
| $CH_2FCl$ | — | 0.15 | 0.65 |

EXAMPLE 9

The procedure of example 1 was repeated except that a catalyst comprising 76.6 g of nickel oxide was employed. The composition of the organic products after scrubbing was as shown in Table 9.

TABLE 9

| Product | Temperature/°C. | | |
|---|---|---|---|
| | 212 | 255 | 312 |
| $CH_2F_2$. | 4.18 | 7.82 | 17.28 |
| $CF_3H$. | 0.29 | 0.02 | 0.05 |
| $CH_4$. | 8.53 | 18.30 | 36.80 |

TABLE 9-continued

| | Temperature/°C. | | |
|---|---|---|---|
| Product | 212 | 255 | 312 |
| $CH_3Cl$. | 0.18 | 1.32 | 9.0 |
| $CH_3F$. | 0.30 | 0.29 | 0.16 |
| $CH_2FCl$ | — | 0.02 | 0.10 |
| $C_2H_6$ | 0.46 | 1.80 | 8.90 |

EXAMPLE 10

The procedure of example 1 was repeated except that the catalyst comprised 100 ml of 5% w/w palladium on eta-alumina spheres. The flow rates of hydrogen and chlorodifluoromethane were 100 ml/minute and 50 ml/minute respectively. The composition of the organic product after scrubbing was as shown in Table 10.

TABLE 10

| | Temperature/°C. | |
|---|---|---|
| Product | 215 | 255 |
| $CH_2F_2$. | 0.24 | 0.96 |
| $CH_3F$. | 0.12 | 0.34 |
| $CH_4$. | 55.13 | 63.16 |
| $CH_3Cl$. | — | 0.03 |

EXAMPLE 11

The procedure of example 10 was repeated but the catalyst comprised 100 mls of 0.5% w/w palladium supported on eta-alumina spheres. The composition of the organic product after scrubbing was as shown in Table 11.

TABLE 11

| | Temperature/°C. | |
|---|---|---|
| Product | 212 | 243. |
| $CH_2F_2$. | 1.94 | 5.80 |
| $CH_3F$. | 0.65 | 0.92 |
| $CH_4$. | 37.93 | 55.12 |
| $CH_3Cl$. | 1.59 | 1.61 |

In all the following examples 12 to 24, the figures given are % yields by volume.

EXAMPLE 12

The procedure of example 1 was repeated except that a 40 mls of a catalyst comprising 8.2% palladium on Norit RX3 extrudate active carbon (supplied by Norit) was employed as the catalyst, and the reactor was constructed of Inconel. The composition of the organic product after scrubbing was as shown in Table 12.

TABLE 12

| Product. | Temperature/°C. | | | | | |
|---|---|---|---|---|---|---|
| % v/v. | 135 | 165 | 199 | 216 | 247 | 260 |
| $CH_2F_2$. | 0.3 | 2.1 | 11.7 | 22.4 | 50.3 | 57.0 |
| $CF_3H$. | 0.0 | 0.0 | 0.02 | 0.04 | 0.2 | 0.3 |
| $CH_4$. | 0.02 | 0.14 | 1.04 | 2.81 | 13.7 | 18.7 |
| $CH_2FCl$. | 0.0 | 0.0 | 0.02 | 0.05 | 0.16 | 0.19 |
| % Conversion. of $CF_2ClH$. | 0.36 | 2.25 | 12.8 | 25.3 | 64.5 | 76.6 |
| % difluoromethane selectivity. | 92.4 | 93.8 | 91.5 | 88.5 | 78.0 | 74.3 |

EXAMPLE 13

The procedure of example 12 was repeated except that a catalyst comprising 10.0% palladium on Norit RX3 extrudate active carbon (supplied by Norit) was employed. The composition of the organic product after scrubbing was as shown in Table 13.

TABLE 13

| Product. | Temperature/°C. | | | | | |
|---|---|---|---|---|---|---|
| % v/v. | 151 | 189 | 217 | 235 | 258 | 282 |
| $CH_2F_2$. | 1.1 | 2.7 | 6.4 | 17.5 | 31.7 | 50.4 |
| $CF_3H$. | 0.0 | 0.0 | 0.01 | 0.04 | 0.1 | 0.2 |
| $CH_4$. | 0.0 | 0.21 | 0.56 | 1.44 | 4.5 | 11.4 |
| $CH_2FCl$. | 0.0 | 0.0 | 0.0 | 0.0 | 0.0 | 0.01 |
| % Conversion. of $CF_2ClH$. | 1.1 | 2.91 | 6.97 | 18.98 | 36.3 | 62.0 |
| % difluoromethane selectivity. | 100.0 | 92.8 | 91.7 | 92.2 | 87.3 | 81.3 |

EXAMPLE 14

The procedure of example 12 was repeated except that a catalyst comprising 11.4% palladium on Grade 208c active carbon (supplied by Sutcliffe Speakman) was employed. The composition of the organic product after scrubbing was as shown in Table 14.

TABLE 14

| Product. | Temperature/°C. | | | | |
|---|---|---|---|---|---|
| % v/v. | 184 | 219 | 259 | 280 | 300 |
| $CH_2F_2$. | 1.27 | 5.53 | 17.04 | 25.1 | 29.68 |
| $CF_3H$. | 0.0 | 0.0 | 0.0 | 0.0 | 0.1 |
| $CH_4$. | 0.63 | 2.63 | 11.5 | 25.7 | 42.81 |
| $CH_2FCl$. | 0.0 | 0.0 | 0.02 | 0.04 | 0.06 |
| % Conversion. of $CF_2ClH$. | 1.9 | 8.16 | 28.56 | 50.84 | 72.65 |

EXAMPLE 15

The procedure of example 12 was repeated except that a catalyst comprising 8.2% palladium on Grade 207c active carbon (supplied by Sutcliffe Speakman) was employed. The composition of the organic product after scrubbing was as shown in Table 15.

TABLE 15

| Product. % v/v. | Temperature/°C. | | | | |
|---|---|---|---|---|---|
| | 162 | 235 | 273 | 291 | 306 |
| $CH_2F_2$. | 0.14 | 3.24 | 11.1 | 16.76 | 21.58 |
| $CF_3H$. | 0.01 | 0.01 | 0.04 | 0.07 | 0.09 |
| $CH_4$. | 0.02 | 0.19 | 8.46 | 16.02 | 25.23 |
| $CH_2FCl$. | 0.0 | 0.0 | 0.02 | 0.05 | 0.09 |
| % Conversion. of $CF_2ClH$. | 0.17 | 3.44 | 19.53 | 32.9 | 46.98 |
| % difluoromethane selectivity. | 86.3 | 72.9 | 56.3 | 50.7 | 45.7 |

EXAMPLE 16

The procedure of example 12 was repeated except that a catalyst comprising 8.2% palladium on SC2 active carbon (supplied by Chemivron) was employed. The composition of the organic product after scrubbing was as shown in Table 16.

TABLE 16

| Product. % v/v. | Temperature/°C. | | | | |
|---|---|---|---|---|---|
| | 172 | 207 | 243 | 261 | 277 | 287 |
| $CH_2F_2$. | 0.44 | 2.64 | 10.4 | 16.72 | 22.6 | 25.8 |
| $CF_3H$. | 0.0 | 0.0 | 0.01 | 0.03 | 0.07 | 0.09 |
| $CH_4$. | 0.08 | 0.82 | 5.81 | 12.43 | 21.3 | 24.3 |
| $CH_2FCl$. | 0.0 | 0.0 | 0.02 | 0.04 | 0.09 | 0.15 |
| % Conversion. of $CF_2ClH$. | 0.52 | 3.46 | 16.24 | 29.22 | 44.1 | 50.3 |
| % Selectivity Difluoromethane. | 85.1 | 76.3 | 63.9 | 57.1 | 51.1 | 51.0 |

EXAMPLE 17

The procedure of example 12 was repeated except that a catalyst comprising 8.2% palladium on SC12 active carbon (supplied by Chemivron) was employed. The composition of the organic product after scrubbing was as shown in Table 17.

TABLE 17

| Product. % v/v. | Temperature/°C. | | | | |
|---|---|---|---|---|---|
| | 179 | 223 | 255 | 266 | 285 |
| $CH_2F_2$. | 0.95 | 6.64 | 16.4 | 21.8 | 29.5 |
| $CF_3H$. | 0.0 | 0.01 | 0.03 | 0.05 | 0.11 |
| $CH_4$. | 0.2 | 2.53 | 9.95 | 15.76 | 27.4 |
| $CH_2FCl$. | 0.0 | 0.0 | 0.03 | 0.06 | 0.15 |
| % Conversion. of $CF_2ClH$. | 1.15 | 8.18 | 26.05 | 37.67 | 56.85 |
| % Selectivity Difluoromethane. | 82.6 | 72.3 | 62.0 | 57.8 | 51.5 |

EXAMPLE 18

The procedure of example 12 was repeated except that a catalyst comprising 8.2% palladium on Grade 207b active carbon (supplied by Sutcliffe Speakman) was employed. The composition of the organic product after scrubbing was as shown in Table 18.

TABLE 18

| Product. % v/v. | Temperature/°C. | | | | |
|---|---|---|---|---|---|
| | 181 | 210 | 244 | 266 | 278 | 291 |
| $CH_2F_2$. | 0.58 | 1.32 | 6.16 | 11.5 | 22.6 | 24.4 |
| $CF_3H$. | 0.02 | 0.01 | 0.01 | 0.04 | 0.02 | 0.01 |
| $CH_4$. | 0.81 | 1.89 | 11.1 | 19.9 | 27.9 | 27.5 |
| $CH_2FCl$. | 0.0 | 0.04 | 0.4 | 0.26 | 0.48 | 0.51 |
| % Conversion. of $CF_2ClH$. | 1.41 | 3.26 | 17.67 | 31.7 | 51.0 | 52.4 |
| % Selectivity Difluoromethane. | 37.4 | 37.7 | 33.7 | 35.4 | 43.3 | 45.3 |

EXAMPLE 19

The procedure of example 12 was repeated except that a catalyst comprising 8.2% palladium on Grade 208c active carbon (supplied by Sutcliffe Speakman) was employed. The composition of the organic product after scrubbing was as shown in Table 19.

TABLE 19

| Product. % v/v. | Temperature/°C. | | | | |
|---|---|---|---|---|---|
| | 178 | 219 | 235 | 253 | 263 | 280 |
| $CH_2F_2$. | 0.8 | 5.57 | 11.0 | 18.1 | 23.1 | 30.9 |
| $CF_3H$. | 0.0 | 0.01 | 0.02 | 0.03 | 0.05 | 0.1 |
| $CH_4$. | 0.15 | 2.46 | 7.0 | 5.48 | 22.1 | 31.1 |
| $CH_2FCl$. | 0.0 | 0.01 | 0.02 | 0.06 | 0.09 | 0.19 |
| % Conversion. of $CF_2ClH$. | 0.95 | 8.05 | 18.04 | 33.67 | 45.3 | 62.3 |
| % Selectivity Difluoromethane. | 84.5 | 69.1 | 60.8 | 53.6 | 50.7 | 49.5 |

EXAMPLE 20

The procedure of example 12 was repeated except that a catalyst comprising 8.2% palladium and 0.1% nickel on Norit RX3 extrudate active (supplied by Norit) carbon was employed. The composition of the organic product aster scrubbing was as shown in Table 20.

TABLE 20

| Product. % v/v. | Temperature/°C. | | | | |
|---|---|---|---|---|---|
| | 193 | 228 | 246 | 267 | 291 | 309 |
| $CH_2F_2$. | 1.79 | 4.6 | 15.9 | 23.1 | 33.2 | 45.0 |
| $CF_3H$. | 0.01 | 0.02 | 0.04 | 0.07 | 0.11 | 0.3 |
| $CH_4$. | 0.17 | 0.41 | 1.85 | 3.48 | 5.4 | 23.0 |
| $CH_2FCl$. | 0.0 | 0.0 | 0.0 | 0.0 | 0.0 | 0.0 |
| % Conversion. of $CF_2ClH$. | 1.97 | 5.03 | 17.79 | 26.65 | 38.7 | 68.3 |
| % Selectivity Difluoromethane. | 90.9 | 91.5 | 89.4 | 86.7 | 85.6 | 66.0 |

EXAMPLE 21

The procedure of example 12 was repeated except that a catalyst comprising 10.0% palladium and 5.0% nickel on Grade 208c active carbon (supplied by Sutcliffe Speakman) was employed, and a stainless steel reactor was used. The composition of the organic product after scrubbing was as shown in Table 21.

TABLE 21

| Product. | Temperature/°C. | | | |
|---|---|---|---|---|
| % v/v. | 169 | 217 | 256 | 283 |
| $CH_2F_2$. | 0.24 | 8.14 | 12.35 | 19.59 |
| $CF_3H$. | 0.0 | 0.1 | 0.1 | 0.2 |
| $CH_4$. | 0.09 | 5.63 | 13.4 | 26.03 |
| $CH_2FCl$. | 0.0 | 0.0 | 0.01 | 0.0 |
| % Conversion. of $CF_2ClH$. | 0.33 | 13.87 | 25.86 | 45.82 |
| % difluoromethane selectivity. | 71.6 | 58.0 | 46.7 | 41.6 |

EXAMPLE 22

The procedure of example 12 was repeated except that the reaction was conducted at a pressure of 7.5 bar. The composition of the organic product after scrubbing was as shown in Table 22.

TABLE 22

| Product. | Temperature/°C. | | |
|---|---|---|---|
| % v/v. | 290 | 315 | 330 |
| $CH_2F_2$. | 24.63 | 31.05 | 29.79 |
| $CF_3H$. | 0.09 | 0.22 | 0.27 |
| $CH_4$. | 1.76 | 2.50 | 2.64 |
| $CH_2FCl$. | 0.06 | 0.06 | 0.07 |
| % Conversion. of $CF_2ClH$. | 26.58 | 33.90 | 32.85 |
| % difluoromethane selectivity. | 92.7 | 92.8 | 90.8 |

EXAMPLE 23

The procedure of example 10 was followed except that dichlorodifluoromethane was used instead of chlorodifluoromethane. The composition of the organic products after scrubbing was as shown in Table 23.

TABLE 23

| Product. | Temperature/°C. | |
|---|---|---|
| % v/v. | 202 | 232 |
| $CF_2ClH$. | 0.28 | 0.12 |
| $CF_2H_2$. | 4.72 | 4.75 |
| $CH_4$. | 62.89 | 72.11 |
| $CH_3Cl$. | 6.19 | 5.68 |
| $CH_2FCl$. | 2.13 | 1.48 |
| % Conversion. of $CF_2Cl_2$. | 76.32 | 84.14 |
| % difluoromethane selectivity. | 6.18 | 5.65 |

EXAMPLE 24

The procedure of example 11 was followed except that dichlorodifluoromethane was used instead of chlorodifluoromethane. The composition of the organic products after scrubbing was as shown in Table 24.

TABLE 24

| Product. | Temperature/°C. | |
|---|---|---|
| % v/v. | 205 | 245 |
| $CF_2ClH$. | 0.23 | 0.43 |
| $CF_2H_2$. | 6.81 | 9.37 |
| $CH_4$. | 40.56 | 47.98 |
| $CH_3Cl$. | 6.64 | 7.62 |
| $CH_2FCl$. | 0.76 | 0.36 |
| % Conversion. of $CF_2Cl_2$. | 55.35 | 65.92 |
| % difluoromethane selectivity. | 12.31 | 14.21 |

We claim:

1. A process for the production of difluoromethane which comprises reacting chlorodifluoromethane with hydrogen at elevated temperature from about 225° to about 400° C. and a pressure ranging from about 2 bar to about 60 bar in the presence of a hydrogenation catalyst comprising palladium carried on an active carbon support wherein palladium is the predominant metal and the % w/w palladium to active carbon is from about 8% w/w to about 20% w/w, the temperature, pressure and catalyst composition being selected such that difluoromethane is produced with a yield of at least 25%, and recycling unreacted starting materials and organic by-products.

2. A process as claimed in claim 1 wherein the loading of palladium on the support is in the range from about 8% to about 15% by weight.

3. A process as claimed in claim 2 wherein the active carbon employed is such that at a temperature of 250° C., atmospheric pressure and a palladium loading of 10% w/w, the yield of difluoromethane is at least 50%.

4. A process as claimed in claim 3 wherein the catalyst comprises one or more metals in addition to palladium carried on an active carbon support.

5. A process as claimed in claim 4 wherein the catalyst comprises a Group VIIIa metal in addition to palladium.

6. A process as claimed in claim 5 wherein the catalyst comprises palladium and nickel carried on an active carbon support.

7. A process as claimed in claim 6 wherein the proportion by weight of palladium and nickel in the catalyst is in the range from about 2:1 to about 500:1.

8. A process as claimed in claim 1 wherein the molar proportion of hydrogen to chlorodifluoromethane is in the range from about 1:1 to about 4:1.

* * * * *